(12) United States Patent
O'Rourke et al.

(10) Patent No.: US 10,256,554 B2
(45) Date of Patent: Apr. 9, 2019

(54) ELECTRICAL CONNECTOR AND METHOD FOR MANUFACTURING AN ELECTRICAL CONNECTOR

(71) Applicant: Cardiac Pacemakers, Inc., St. Paul, MN (US)

(72) Inventors: John O'Rourke, Co. Tipperary (IE); James Fouhy, Co Cork (IE); Michael J. Kane, Roseville, MN (US); James Michael English, Cahir (IE); Arthur J. Foster, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 9 days.

(21) Appl. No.: 15/065,065

(22) Filed: Mar. 9, 2016

(65) Prior Publication Data

US 2016/0268706 A1    Sep. 15, 2016

Related U.S. Application Data

(60) Provisional application No. 62/132,337, filed on Mar. 12, 2015.

(51) Int. Cl.
*A61N 1/00* (2006.01)
*H01R 4/48* (2006.01)
(Continued)

(52) U.S. Cl.
CPC ............... *H01R 4/48* (2013.01); *A61N 1/056* (2013.01); *A61N 1/362* (2013.01); *A61N 1/3754* (2013.01);
(Continued)

(58) Field of Classification Search
USPC .......................................................... 607/37
See application file for complete search history.

(56) References Cited

U.S. PATENT DOCUMENTS

| 4,033,654 A | 7/1977 | Ross |
| 5,413,595 A | 5/1995 | Stutz, Jr. |

(Continued)

FOREIGN PATENT DOCUMENTS

| CN | 101141034 A | 3/2008 |
| CN | 107431300 A | 12/2017 |

(Continued)

OTHER PUBLICATIONS

"Additive manufacturing", Roland Berger Strategy Consultant (EOS); Munich, (Nov. 2013), 1-33.

(Continued)

*Primary Examiner* — Nicole F Johnson
(74) *Attorney, Agent, or Firm* — Schwegman Lundberg & Woessner, P.A.

(57) ABSTRACT

An electrical connector for detachably connecting an electrical lead to an implantable medical device includes a conductive housing and a plurality of spring contacts. The conductive housing extends from a proximal end to a distal end. The conductive housing has an interior surface forming a hollow cylinder. The plurality of spring contacts projects from the interior surface of the conductive housing and toward the proximal end. The plurality of spring contacts is at least partially contained within the conductive housing and configured to form an electrical connection to an electrical lead inserted within the conductive housing. The conductive housing and the plurality of spring contacts are integrally formed by an additive manufacturing process such that the electrical connector is a unitary structure.

14 Claims, 7 Drawing Sheets

(51) Int. Cl.
*H01R 13/187* (2006.01)
*H01R 43/16* (2006.01)
*H01R 43/18* (2006.01)
*A61N 1/05* (2006.01)
*A61N 1/362* (2006.01)
*A61N 1/375* (2006.01)
*B33Y 80/00* (2015.01)

(52) U.S. Cl.
CPC .......... *H01R 13/187* (2013.01); *H01R 43/16* (2013.01); *H01R 43/18* (2013.01); *A61N 1/3752* (2013.01); *B33Y 80/00* (2014.12); *H01R 2201/12* (2013.01)

(56) References Cited

U.S. PATENT DOCUMENTS

| | | | |
|---|---|---|---|
| 5,730,628 | A | 3/1998 | Hawkins |
| 6,878,013 | B1 | 4/2005 | Behan |
| 7,195,523 | B2 | 3/2007 | Naviaux |
| 7,590,451 | B2 | 9/2009 | Tronnes et al. |
| 7,890,175 | B1 | 2/2011 | Rey et al. |
| 8,328,587 | B2 | 12/2012 | Dilmaghanian |
| 8,428,724 | B2 | 4/2013 | Sage |
| 8,437,855 | B2 | 5/2013 | Sjostedt et al. |
| 2005/0027327 | A1* | 2/2005 | Ries .................. A61N 1/3752 607/37 |
| 2008/0255631 | A1 | 10/2008 | Sjostedt et al. |
| 2011/0270363 | A1 | 11/2011 | Schramm et al. |

FOREIGN PATENT DOCUMENTS

| | | |
|---|---|---|
| FR | 2970874 A1 | 8/2012 |
| JP | 2007500535 A | 1/2007 |
| JP | 2012532671 A | 12/2012 |
| JP | 2014505550 A | 3/2014 |
| WO | WO-2016145029 A1 | 9/2016 |

OTHER PUBLICATIONS

"Australian Application Serial No. 2016229809, First Examination Report dated Feb. 19, 2018", 3 pgs.

"European Application Serial No. 16726987.7, Response filed Mar. 13, 2018 to Communication Pursuant to Rules 161(1) and 162 EPC dated Oct. 26, 2017", 16 pgs.

"International Application Serial No. PCT/US2016/021485, International Preliminary Report on Patentability dated Sep. 21, 2017", 9 pgs.

"International Application Serial No. PCT/US2016/021485, International Search Report dated Jul. 13, 2016", 4 pgs.

"International Application Serial No. PCT/US2016/021485, Written Opinion dated Jul. 13, 2016", 7 pgs.

"Australian Application Serial No. 2016229809, Response filed Aug. 6, 2018 to First Examination Report dated Feb. 19, 2018", 8 pgs.

"Chinese Application Serial No. 201680015030.7, Office Action dated Sep. 29, 2018", w/ English translation, 20 pgs.

"Japanese Application Serial No. 2017-547966, Office Action dated Oct. 23, 2018", w/ English Translation, 9 pgs.

\* cited by examiner

ELECTRICAL CONNECTOR AND METHOD FOR MANUFACTURING AN ELECTRICAL CONNECTOR

TECHNICAL FIELD

The application claims the benefit of priority under 35 U.S.C. § 119(e) of U.S. Provisional Patent Application Ser. No. 62/132,337, filed on Mar. 12, 2015, which is herein incorporated by reference in its entirety.

TECHNICAL FIELD

The present invention relates to electrical connectors and methods for manufacturing electrical connectors. More specifically, the invention relates to electrical connectors suitable for use with an implantable medical device.

BACKGROUND

Implantable medical devices, such as implantable cardioverter defibrillators, pacemakers, and neuromodulation devices, are used in a variety of therapeutic applications. In some applications, one or more implantable electrical leads are employed to deliver therapy from an implanted medical device to tissues within a body. The electrical lead may have one or more electrodes near a distal end of the electrical lead electrically connected to terminal pin contacts near a proximal, or terminal, end of the electrical lead. The terminal end of the electrical lead may be inserted into ports in a lead connector block of the implanted medical device. The lead connector block may include an electrical connector that contacts a terminal pin contact of the electrical lead to electrically connect the implanted medical device to the electrical lead. The electrical connection is detachable so that the electrical lead may be coupled and decoupled as necessary.

The electrical connectors within the lead connector block may include spring contacts to provide the electrical connection to the terminal pin contacts once the terminal end of the electrical lead is inserted into the lead connector block. A minimum level of normal, or contact, force must be provided by the spring contacts to ensure a reliable electrical connection between the electrical connector and the electrical lead. Flat, or leaf, spring contacts may be used, but such flat, or leaf, spring contacts may be overstressed or bent, particularly with repeated coupling and decoupling between the electrical lead and the lead connector block, leading to a normal force that is lower than that necessary to provide a reliable electrical connection.

SUMMARY

In Example 1, an electrical connector for detachably connecting an electrical lead to an implantable medical device includes a conductive housing and a plurality of spring contacts. The conductive housing extends from a proximal end to a distal end and has an interior surface forming a hollow cylinder. The plurality of spring contacts projects from the interior surface of the conductive housing and toward the proximal end. The plurality of spring contacts is at least partially contained within the conductive housing and configured to form an electrical connection to an electrical lead inserted within the conductive housing. The conductive housing and the plurality of spring contacts are integrally formed by an additive manufacturing process such that the electrical connector is a unitary structure.

In Example 2, the electrical connector of Example 1, wherein the each spring contact of the plurality of spring contacts has a length extending from the conductive housing to a tip of the spring contact, and an average cross-sectional aspect ratio along its length, wherein the average cross-sectional aspect ratio is from 1 to 3.

In Example 3, the electrical connector of any of Examples 1-2, wherein the average cross-sectional aspect ratio is 1.

In Example 4, the electrical connector of any of Examples 1-3, wherein the additive manufacturing process is a powder bed fusion process employing a metal powder, wherein the metal powder is an alloy including about 34 to 36 wt % nickel, about 19 to 21 wt. % chromium, about 9 to 11 wt. % molybdenum, and about 32 to 38 wt. % cobalt or consisting essentially of 34 to 36 wt. % nickel, 19 to 21 wt % chromium, 9 to 11 wt. % molybdenum, and 32 to 38 wt. % cobalt.

In Example 5, the electrical connector of any of Examples 1-4, wherein each spring contact of the plurality of spring contacts has a length extending from the conductive housing to a tip of the spring contact, and has an elliptical cross-sectional shape along at least a portion of its length.

In Example 6, the electrical connector of any of Examples 1-5, wherein the plurality of spring contacts includes at least twenty spring contacts.

In Example 7, the electrical connector of any of Examples 1-6, wherein the conductive housing further includes a distal portion adjacent to the distal end, and a proximal portion adjacent to the proximal end and spaced apart from the distal portion. The plurality of spring contacts projects from the interior surface of the distal portion of the conductive housing and toward the proximal end. The proximal portion is connected to the distal portion by the plurality of spring contacts.

In Example 8, the electrical connector of any of Examples 1-7, wherein each spring contact of the plurality of spring contacts is canted or spirals at least partially around an axis of the conductive housing.

In Example 9, an implantable medical device includes a case and a lead connector block. The case includes operational circuitry for providing therapy and an electrical feedthrough electrically connected to the circuit. The lead connector block is attached to the case at the electrical feedthrough. The lead connector block is configured to receive at least one terminal pin of an electrical lead. The lead connector block includes an electrical connector according to any of Examples 1-8 electrically connected to the electrical feedthrough for detachably connecting the electrical lead to the operational circuitry.

In Example 10, a method for manufacturing an electrical connector for detachably connecting an electrical lead to an implantable medical device includes performing an additive manufacturing process to form an electrical connector. The electrical connector includes a conductive housing having an interior surface extending from a proximal end to a distal end forming a hollow cylinder. The electrical connector also includes a plurality of spring contacts projecting from the interior surface of the conductive housing and toward the proximal end, the plurality of spring contacts at least partially contained within the conductive housing and configured to form an electrical connection to an electrical lead inserted within the conductive housing. The conductive housing and the plurality of spring contacts are integrally formed by the additive manufacturing process such that the electrical connector is a unitary structure.

In Example 11, the method of Example 10, further comprising finishing at least a portion of a surface of the electrical connector.

In Example 12, the method of Example 11, wherein finishing includes at least one of electrochemical polishing, mechanical polishing, electro plasma polishing, glazing, wet blasting, grit blasting, wire electrical discharge machining, and passivating techniques.

In Example 13, the method of any of Examples 10-12, wherein the additive manufacturing process is a powder bed fusion process.

In Example 14, the method of Example 13, wherein the powder bed fusion process is a micro laser sintering process employing a metal powder having an average particle size of less than 10 micrometers.

In Example 15, the method of Example 14, wherein the metal powder has an average particle size of less than 5 micrometers.

In Example 16, the method of any of Examples 10-15, wherein the each spring contact of the plurality of spring contacts has a length extending from the conductive housing to a tip of the spring contact, and an average cross-sectional aspect ratio along its length, wherein the average cross-sectional aspect ratio is from 1 to 3.

In Example 17, the method of Example 16, wherein the average cross-sectional aspect ratio is 1.

In Example 18, the method of any of Examples 10-17, wherein each spring contact of the plurality of spring contacts has a length extending from the conductive housing to a tip of the spring contact, and has an elliptical cross-sectional shape along at least a portion of its length.

In Example 19, the method of any of Examples 10-18, wherein the plurality of spring contacts includes at least twenty spring contacts.

In Example 20, the method of any of Examples 10-19, wherein each spring contact of the plurality of spring contacts is canted or spirals at least partially around an axis of the conductive housing.

In Example 21, an electrical connector for detachably connecting an electrical lead to an implantable medical device includes a conductive housing and a plurality of spring contacts. The conductive housing extends from a proximal end to a distal end and has an interior surface forming a hollow cylinder. The plurality of spring contacts projects from the interior surface of the conductive housing and toward the proximal end. The plurality of spring contacts is at least partially contained within the conductive housing and configured to form an electrical connection to an electrical lead inserted within the conductive housing. The conductive housing and the plurality of spring contacts are integrally formed by an additive manufacturing process such that the electrical connector is a unitary structure.

In Example 22, the electrical connector of Example 21, wherein the each spring contact of the plurality of spring contacts has a length extending from the conductive housing to a tip of the spring contact, and an average cross-sectional aspect ratio along its length, wherein the average cross-sectional aspect ratio is about 1 to about 3.

In Example 23, the electrical connector of any of Examples 21-22, wherein the average cross-sectional aspect ratio is about 1.

In Example 24, the electrical connector of any of Examples 21-23, wherein the additive manufacturing process is a powder bed fusion process employing a metal powder, wherein the metal powder is an alloy including about 34 to 36 wt. % nickel, about 19 to 21 wt. % chromium, about 9 to 11 wt. % molybdenum, and about 32 to 38 wt. % cobalt.

In Example 25, the electrical connector of any of Examples 21-24, wherein each spring contact of the plurality of spring contacts has a length extending from the conductive housing to a tip of the spring contact, and has an elliptical cross-sectional shape along at least a portion of its length.

In Example 26, the electrical connector of any of Examples 21-24, wherein each spring contact of the plurality of spring contacts has a length extending from the conductive housing to a tip of the spring contact, and has a triangular cross-sectional shape along at least a portion of its length.

In Example 27, the electrical connector of any of Examples 21-26, wherein the plurality of spring contacts includes at least twenty spring contacts.

In Example 28, the electrical connector of any of Examples 21-27, wherein the conductive housing further includes a distal portion adjacent to the distal end, and a proximal portion adjacent to the proximal end and spaced apart from the distal portion. The plurality of spring contacts projects from the interior surface of the distal portion of the conductive housing and toward the proximal end. The proximal portion is connected to the distal portion by the plurality of spring contacts.

In Example 29, the electrical connector of any of Examples 21-28, wherein each spring contact of the plurality of spring contacts is canted or spirals at least partially around an axis of the conductive housing.

In Example 30, a method for manufacturing an electrical connector for detachably connecting an electrical lead to an implantable medical device includes performing an additive manufacturing process to form an electrical connector. The electrical connector includes a conductive housing having an interior surface extending from a proximal end to a distal end forming a hollow cylinder. The electrical connector also includes a plurality of spring contacts projecting from the interior surface of the conductive housing and toward the proximal end, the plurality of spring contacts at least partially contained within the conductive housing and configured to form an electrical connection to an electrical lead inserted within the conductive housing. The conductive housing and the plurality of spring contacts are integrally formed by the additive manufacturing process such that the electrical connector is a unitary structure.

In Example 31, the method of Example 30, further comprising finishing at least a portion of a surface of the electrical connector.

In Example 32, the method of Example 31, wherein finishing includes at least one of electrochemical polishing, mechanical polishing, electro plasma polishing, glazing, wet blasting, grit blasting, wire electrical discharge machining, and passivating techniques.

In Example 33, the method of any of Examples 30-32, wherein the additive manufacturing process is a powder bed fusion process.

In Example 34, the method of Example 33, wherein the powder bed fusion process is a micro laser sintering process employing a metal powder having an average particle size of less than about 10 micrometers.

In Example 35, the method of Example 34, wherein the metal powder has an average particle size of about 5 micrometers.

In Example 36, an implantable medical device includes a case and a lead connector block. The case includes operational circuitry for providing therapy, and an electrical feedthrough electrically connected to the circuit. The lead connector block is attached to the case at the electrical feedthrough. The lead connector block is configured to receive at least one terminal pin of an electrical lead. The terminal pin includes at least one terminal pin contact. The lead connector block includes an electrical connector electrically connected to the electrical feedthrough for detachably connecting the electrical lead to the operational circuitry. The electrical connector includes a conductive housing and a plurality of spring contacts. The conductive housing extends from a proximal end to a distal end and has an interior surface forming a hollow cylinder. The plurality of spring contacts projects from the interior surface of the conductive housing and toward the proximal end. The plurality of spring contacts is at least partially contained within the conductive housing and configured to form an electrical connection to an electrical lead inserted within the conductive housing. The conductive housing and the plurality of spring contacts are integrally formed by an additive manufacturing process such that the electrical connector is a unitary structure.

In Example 37, the device of Example 36, wherein each spring contact of the plurality of spring contacts has a length extending from the conductive housing to a tip of the spring contact, and an average cross-sectional aspect ratio along its length, wherein the average cross-sectional aspect ratio is about 1 to about 3.

In Example 38, the device of any of Examples 36-37, wherein the additive manufacturing process is a powder bed fusion process employing a metal powder, wherein the metal powder is an alloy including about 34 to 36 wt. % nickel, about 19 to 21 wt. % chromium, about 9 to 11 wt. % molybdenum, and about 32 to 38 wt. % cobalt.

In Example 39, the device of any of Examples 36-38, wherein each spring contact of the plurality of spring contacts has a length extending from the conductive housing to a tip of the spring contact, and has an elliptical cross-sectional shape along at least a portion of its length.

In Example 40, the device of any of Examples 36-39, wherein the plurality of spring contacts includes at least twenty spring contacts.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
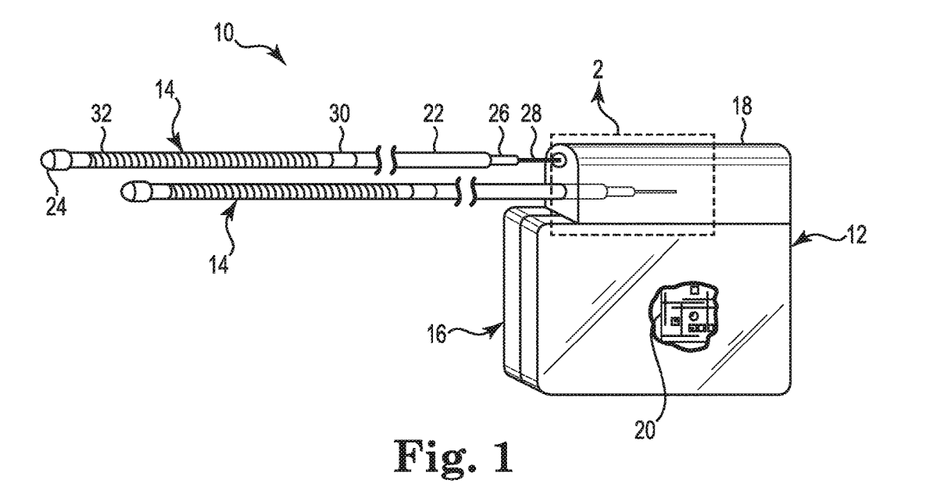
FIG. 1 is a schematic view of a medical system including an implantable medical device including an electrical connector in accordance with embodiments of the present invention.

FIG. 1 provides an illustrative, but non-limiting, example of a medical application using an implantable medical device and an implantable electrical lead electrically connected to the implantable medical device. The application is illustrative only, as implantable medical devices incorporating embodiments of the present invention may be used in a variety of medical applications and for a variety of purposes.

FIG. 1 is a schematic view of a medical system 10 including an electrical connector in accordance with embodiments of the present invention. FIG. 1 shows that the medical system 10 may include an implantable medical device (IMD) 12 and at least one electrical lead 14. The IMD 12 may include a case 16 and a lead connector block 18. The case 16 may include operational circuit 20. In the embodiment of FIG. 1, two electrical leads 14 are illustrated, one shown coupled to the lead connector block 18, and another shown decoupled to the lead connector block 18. Each of the electrical leads 14 may include a proximal or terminal end 22, a distal end 24, a first terminal contact 26, a second terminal contact 28, a first electrode 30, and a second electrode 32. In the embodiment of FIG. 1, the first terminal contact 26 and the second terminal contact 28 may both be located proximate to the proximal or terminal end 22. The first electrode 30 and the second electrode 32 may both be located proximate to the distal end 24 and be electrically connected to the first terminal contact 26 and the second terminal contact 28, respectively, by conductors (not shown) running within each of the electrical leads 14.

The first terminal contact 26 and the second terminal contact 28 of each of electrical leads 14 may be coupled to the lead connector block 18 by an electrical connector embodiment within the lead connector block 18, as described below. Once coupled, the operational circuitry 20 within case 16 may be electrically connected to the first terminal contact 26 and the second terminal contact 28 of each of electrical leads 14. So connected, operational circuitry 20 may be configured to provide electro stimulation therapy in the form of electrical pulses delivered by at least one of the first electrode 26 or the second electrode 28 of the electrical leads 14. The operational circuitry 20 may also employ at least one of the first electrode 26 or the second electrode 28 of the electrical leads 14 to sense conditions within the body that indicate the effectiveness of the therapy and/or indicate a need for additional therapy. The therapy may be in the form of electrical pulses, for example, defibrillation, cardioversion, heart pacing, or neuromodulation.

In the embodiment of FIG. 1, the case 16 may be made of a biocompatible conductor, such as titanium. Each of the electrical leads 14 may be made of insulating material along most of its structure, for example, polyurethane or silicone. The insulating structure separates and isolates one or more terminal contacts, such as the first terminal contact 26 and the second terminal contact 28, or electrodes, such as the first electrode 30 and the second electrode 32, from each other. In the illustrated embodiment, the first electrode 30 is illustrated as a plate-type electrode and the second electrode 32 is illustrated as a coil electrode extending circumferentially about the electrical lead 14. However, it is understood that other electrode shapes, including flat plates and non-circumferentially extending electrodes, may be used. The first terminal contact 26, the second terminal contact 28, the first electrode 30, and the second electrode 32 may also be made of a biocompatible conductor, such as titanium.

Figure 2:
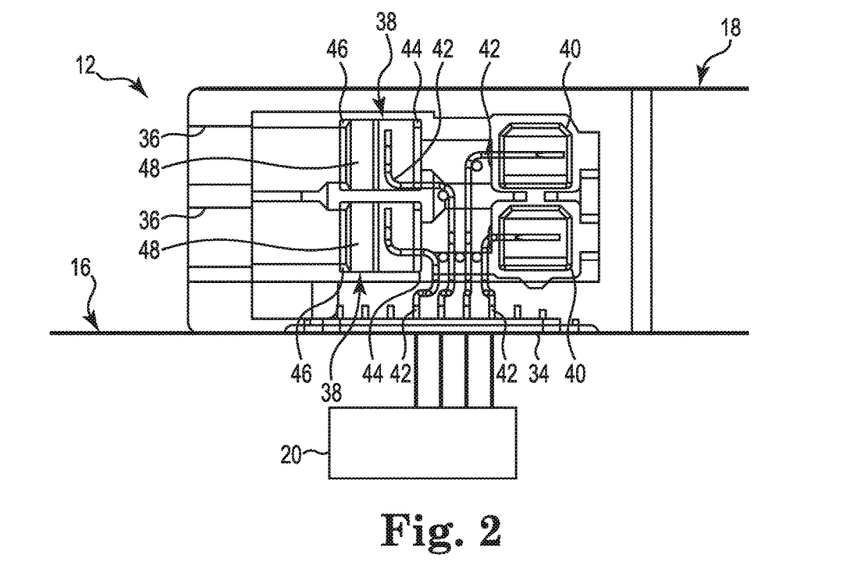
FIG. 2 is a schematic side view of a portion of the implantable medical device of FIG. 1.

FIG. 2 is a schematic side view of a portion of the implantable medical device 12 of FIG. 1. FIG. 2 shows a portion of the IMD 12 including a portion of the case 16 and the lead connector block 18. As shown in FIG. 2, the case 16 may further include an electrical feedthrough 34 providing a connection between the operational circuitry 20 and the lead connector block 18. The lead connector block 18 may include at least one terminal pin receiving port 36 (two shown), at least one first electrical connector 38 (two shown), at least one second electrical connector 40, and a plurality of connecting wires 42. The terminal pin receiving port 36 is an opening in the lead connector block 18 into which the proximal end 22 may be received when coupling the electrical lead 14 to the lead connector block 18. The terminal pin receiving port 36, the first electrical connector 38, and the second electrical connector 40 may be axially aligned. Each of the first electrical connectors 38 includes a proximal end 44, a distal end 46, and an exterior surface 48 extending from the proximal end 44 to the distal end 46. The distal end 46 is nearest the terminal pin receiving port 36.

The plurality of connecting wires 42 may electrically connect the exterior surface 48 of each of the first electrical connectors 38, and an external surface of each of the second electrical connectors 40, to operational circuitry 20 by way of the electrical feedthrough 34. Considering FIGS. 1 and 2 together, when the proximal end 22 of the electrical lead 14 is coupled to the lead connector block 18, the first terminal contact 26 may be in electrical contact with the first electrical connector 38, and the second terminal contact 28 may be in electrical contact with the second terminal contact 40. So coupled, the operational circuitry 20 within case 16 may be electrically connected to the first terminal contact 26 and the second terminal contact 28 of the electrical lead 14.

Figure 3A:
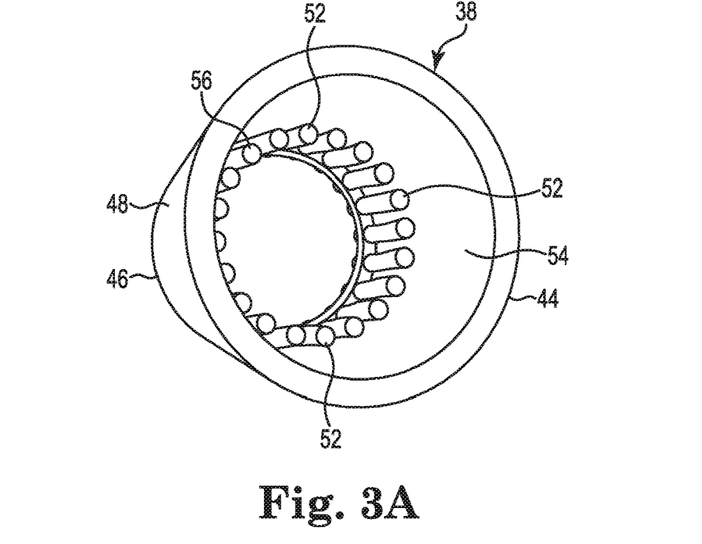
FIGS. 3A and 3B are a proximal end view and a cross-sectional view, respectively, of an electrical connector in accordance with embodiments of the present invention.
Figure 3B:
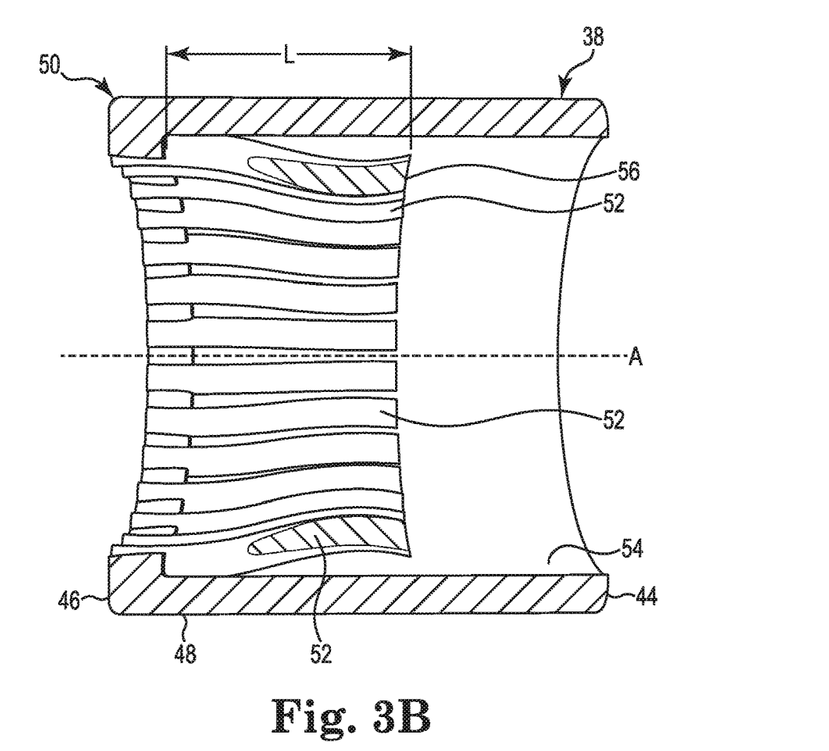

FIGS. 3A and 3B are a proximal end view and a cross-sectional view, respectively, of the electrical connector 38 shown above in reference to FIG. 2. Considering FIGS. 3A and 3B together, the electrical connector 38 may include a housing 50 and a plurality of spring contacts 52. The housing 50 may include the exterior surface 48 (which is also the exterior surface 48 of the electrical connector 38 as noted above) and an interior surface 54. The interior surface 54 may be in the form of a hollow cylinder having an axis A. The spring contacts 52 may project from the interior surface 54 of housing 50 and toward the proximal end 44. As shown in FIGS. 3A and 3B, the spring contacts 52 may be contained within the housing 50. In other embodiments, the spring contacts 52 may project beyond the proximal end 44 and, thus, be partially contained within the housing 50.

Each of the spring contacts 52 illustrated in FIGS. 3A and 3B have a length L extending from the housing 50 to a tip 56 of the spring contact 52. Each of the spring contacts 52 has an average cross-sectional aspect ratio along its length L. The cross-sectional aspect ratio at any point along the length L is the ratio of a largest cross-sectional dimension to a smallest cross-sectional dimension in a plane intersecting the spring contact 52 at the point along length L, the plane being perpendicular to axis A (the axis A being a central axis of the housing 50). In some embodiments, the cross-sectional shape at most points along the length L may be approximately circular. A circular cross-section has a cross-sectional aspect ratio of 1 and is the lowest possible cross-sectional ratio. Other embodiments may have other cross-sectional shapes such as, for example, elliptical, rectangular, or triangular. In some embodiments, the average cross-sectional aspect ratio along the length L of the spring contacts 52 may be about 1. In other embodiments, the average cross-sectional aspect ratio along the length L of the spring contacts 52 may be about 3. In some embodiments, the average cross-sectional aspect ratio along the length L of the spring contacts 52 may be between 1 and 3.

Figure 4A:
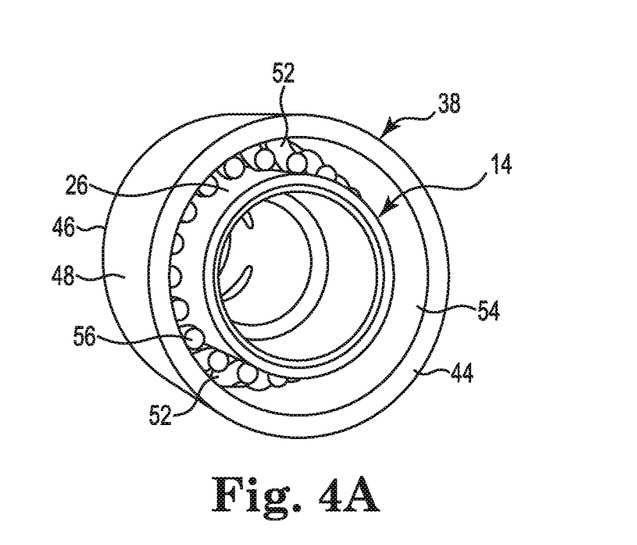
FIGS. 4A and 4B are a proximal end view and a cross-sectional view, respectively, of the electrical connector shown in FIGS. 3A and 3B, illustrating contact between the electrical connector and a terminal pin contact of an implantable medical lead.
Figure 4B:
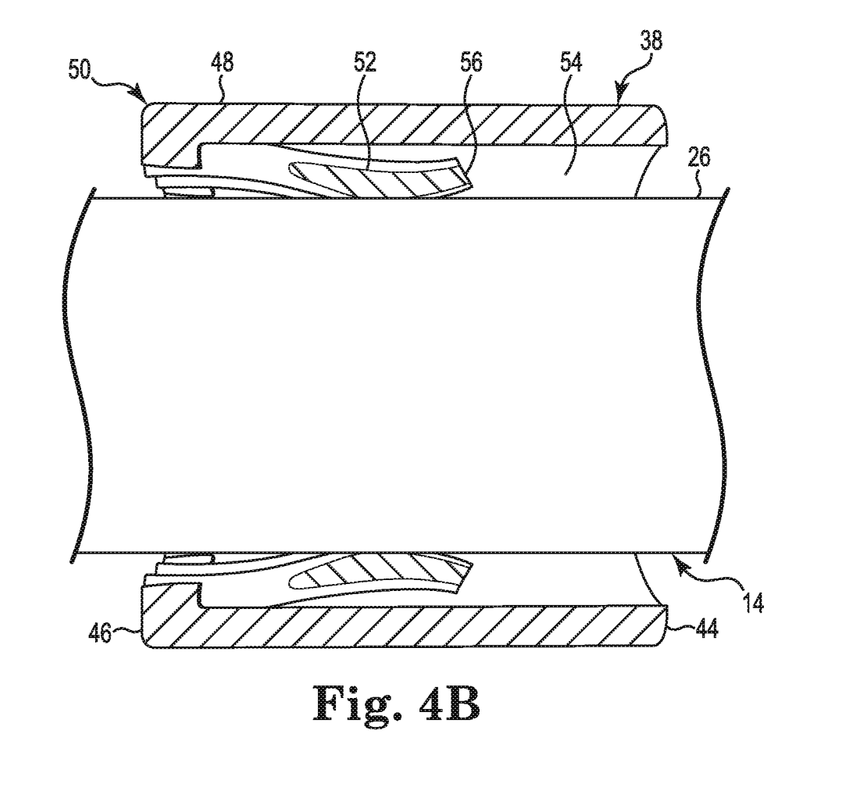

FIGS. 3A and 3B illustrate the electrical connector 38 in a condition in which the electrical lead 14 is not coupled to the lead connector block 18. That is, the spring contacts 52 are in a relaxed state and are extending at least partially toward the axis A of the housing 50. In contrast, FIGS. 4A and 4B are a proximal end view, and a cross-sectional view, respectively, of the electrical connector 38 illustrating a condition in which the electrical lead 14 is coupled to the lead connector block 18 forming an electrical connection between the electrical connector 38 and the first terminal contact 26 of electrical lead 14. In a relaxed state, a portion of each of the spring contacts 52 along the length L extends toward the axis A such that a radial distance from the axis A to the portion of the spring contact 52 is less than a radius of the electrical lead 14 at the first terminal contact 26. This ensures that when the electrical lead 14 is coupled to the lead connector block 18, the first terminal contact 26 pushes against the plurality of spring contacts 52, as shown in FIGS. 4A and 4B. Due to the resilient nature of the spring contacts 52, they move radially outward from the axis A, producing a normal force between the spring contacts 52 and the first terminal contact 26. In this way, embodiments of the electrical connector 38 form an electrical connection between the electrical lead 14 and the IMD 12.

Embodiments of the electrical connector 38 in which the spring contacts 52 have an average cross-sectional aspect ratio along their length L that is relatively low, such as 1, or 3, or between about 1 and about 3, may be more resilient to repeated coupling and decoupling between the electrical lead 14 and the lead connector block 18 compared with flat, or leaf, spring contacts which may have higher average cross-sectional aspect ratios along their lengths. The lower average cross-sectional aspect ratio for embodiments of the electrical connector 38 may make it less likely that any of the spring contacts 52 may be permanently deformed by being physical overstressed. Being more resilient to repeated coupling and decoupling may mean that in such embodiments of the electrical connector 38, the spring contacts 52 are able to provide a more consistent normal force between the spring contacts 52 and the first terminal contact 26.

Embodiments of the electrical connector 38 may include many more of the spring contacts 52 than would be possible for flat, or leaf, spring due to the relatively low average cross-sectional aspect ratio along their length L of the spring contacts 52. In some embodiments, the electrical connector 38 may include at least twenty spring contacts 52. In other embodiments, the electrical connector 38 may include at least twenty-five spring contacts 52. A greater number of spring contacts 52 may provide a lower resistance connection between the electrical connector 38 and the first terminal contact 26.

Embodiments of the electrical connector 38, including the housing 50 and the plurality of spring contacts 52 may be integrally formed such that the electrical connector 38 is a unitary structure. Such embodiments of the electrical connector 38 may be formed by an additive manufacturing process, such as, a powder bed fusion process as described below in reference to FIG. 8, or by other additive manufacturing processes, for example, directed energy deposition (e.g. laser engineered net shaping (LENS)). Embodiments in which the electrical connector 38 is integrally formed may have significant advantages over electrical connectors in which a housing and spring contacts are separate components. One advantage may be in the reduction in assembly complexity and cost by having a single component electrical connector instead of an electrical connector having two or more components. Another advantage is the removal of a physical and electrical contact interface between the housing and the spring contacts. Electrical connectors in which the housing and spring contacts are separate components may include a physical interface between the two components across which an electrical connection must be maintained. Such an interface may add a resistance to the electrical connection between the electrical lead 14 and the operational circuitry 20 due to native oxide layers at the contacting metal surfaces and the imperfectly matching surface topography presented by the contacting metal surface, which may prevent complete physical and electrical contact between the surfaces. Such native oxide layers and contact surface topography may be random and uncontrolled in their effect, leading not only a higher electrical connector resistance, but a more variable electrical connector resistance as well. Embodiments of the electrical connector 38 having a unitary structure do not have a physical interface between the housing 50 and the spring contacts 52. Thus, such embodiments of the electrical connector 38 may advantageously present a lower electrical connector resistance and a more consistent connection between the electrical lead 14 and the IMD 12.

The unitary structure of the housing 50 and the plurality of spring contacts 52 may be made of a conductive metal such as, for example, nickel/cobalt/chromium alloys, stainless steels (e.g., 316L), platinum/iridium alloys, silver, or titanium, or a combination thereof.

In the embodiments of the electrical connector 38 described above and shown in FIGS. 4A, and 4B, each of the spring contacts 52 may be coplanar with the axis A; that is, a single plane may contain both a center of each spring contact 52 along its length L, and the axis A. In such embodiments, an intersection between each of the spring contacts 52 and the first terminal contact 26 may be a line parallel to the axis A. In other embodiments, the spring contacts may be canted such that an intersection between each of the spring contacts and the first terminal contact 26 may be a line that is not parallel to the axis of the housing. In other embodiments, the spring contacts may be spiraled such that an intersection between each of the spring contacts and the first terminal contact 26 may be a curve. Thus, there is no spiral or cant shown with respect to the spring contacts 52 of the electrical connector 38. Embodiments having a spiral or cant with respect to the spring contacts are described below.

Figure 5A:
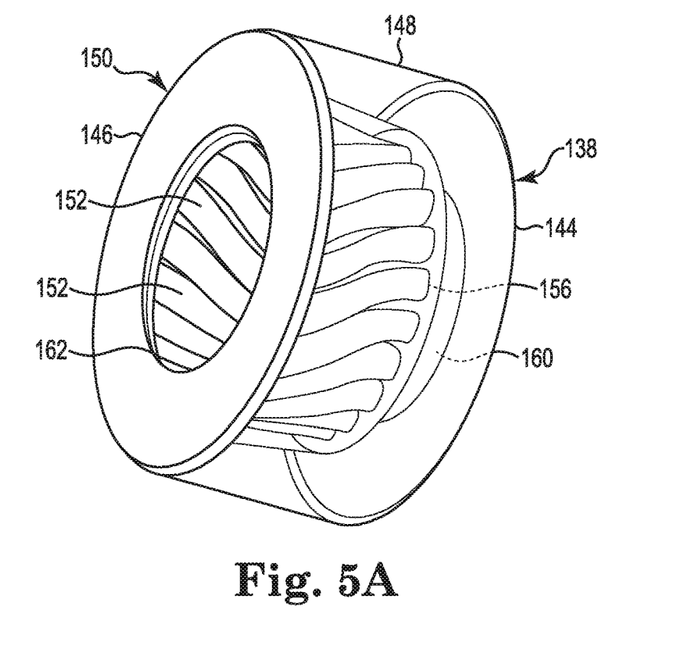
FIGS. 5A and 5B are a distal end view, and a cross-sectional view, respectively, of another electrical connector in accordance with embodiments of the present invention.
Figure 5B:
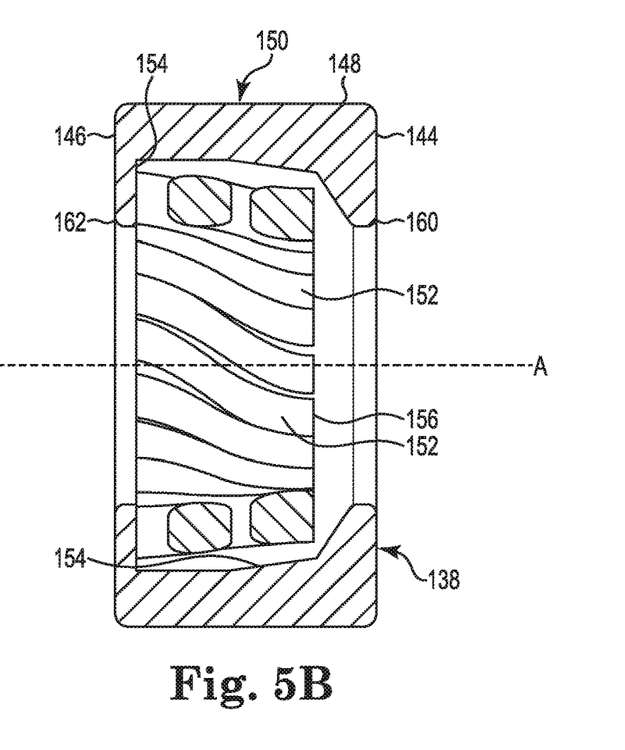

FIGS. 5A and 5B are a distal end view and a cross-sectional view, respectively, of another electrical connector having spring contacts that are spiraled, in accordance with embodiments of the present invention. Together, FIGS. 5A and 5B show an electrical connector 138 including a proximal end 144, a distal end 146, a housing 150, and a plurality of spring contacts 152. In FIG. 5A, a portion of the housing 150 is illustrated in outline so that the details of the spring contacts 152 may be more easily shown. The housing 150 may include an exterior surface 148 and the interior surface 154. The interior surface 154 may be in the form of a hollow cylinder having an axis A. The spring contacts 152 may project from the interior surface 154 of housing 150 and toward the proximal end 144 to a tip 156. As shown in FIGS. 5A and 5B, the spring contacts 152 may be spiraled at least partially around the axis A of housing 150. The spiraling of the spring contacts 152 relative to the axis A may result in a longer physical contact region between each of the spring contacts 152 and the first terminal contact 26 inserted into the electrical connector 138. Also, the spiraling of the spring contacts 152 may result in a larger deflection range over which the normal pressure applied by the spring contacts 152 is consistent. This feature might produce a more consistent contact resistance between the spring contacts 152 and the first terminal contact 26 in cases where a diameter of the first terminal contact 26 varies between the electrical leads 14.

As further shown in FIGS. 5A, and 5B, in some embodiments of the electrical connector 138, the housing 150 may further include a proximal end shoulder 160 and/or a distal end shoulder 162. The proximal end shoulder 160 may project radially inward toward the axis A at the proximal end 144. The distal shoulder 162 may project radially inward toward the axis A at the distal end 146. The proximal end shoulder 160 and the distal end shoulder 162 may help align the electrical lead 14 within the electrical connector 138 and may prevent overstressing the spring contacts 152. As with the spring contacts 52 described above for electrical connector 38, the spring contacts 152 may have an average cross-sectional aspect ratio along their length that is relatively low, such as 1 or 3, or between about 1 and about 3, and are thus more resistant to damage from being overstressed. The electrical connector 138 with the spring contacts 152 having an average cross-sectional aspect ratio along their length L that is relatively low, in combination with the proximal end shoulder 160 and/or the distal end shoulder 162, may be advantageously resistant to damage to the spring contacts 152.

Embodiments of the electrical connector 138, including the housing 150 and the plurality of spring contacts 152 may be integrally formed such that the electrical connector 138 is a unitary structure. Such embodiments of the electrical connector 138 may be formed by an additive manufacturing process, such as, a powder bed fusion process as described below in reference to FIG. 8, or by another additive manufacturing process.

Figure 6A:
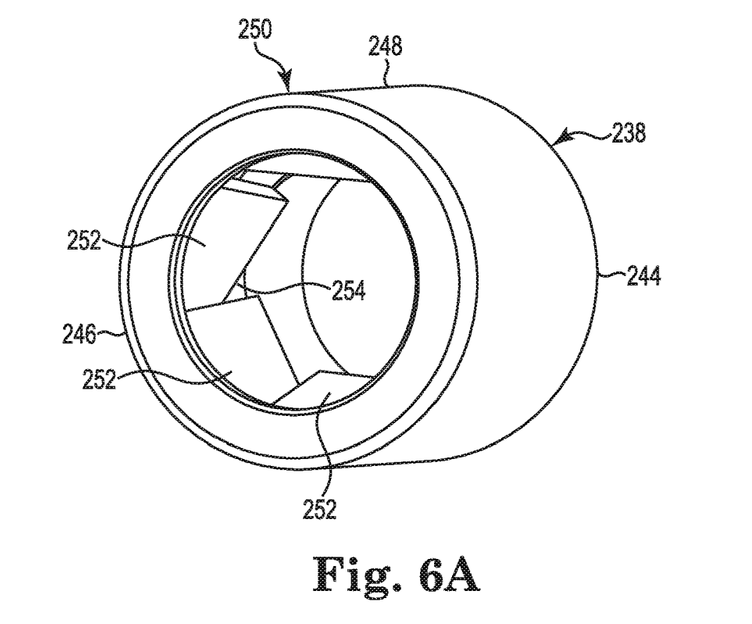
FIGS. 6A and 6B are a distal end view and a cross-sectional view, respectively, of another electrical connector in accordance with embodiments of the present invention.
Figure 6B:
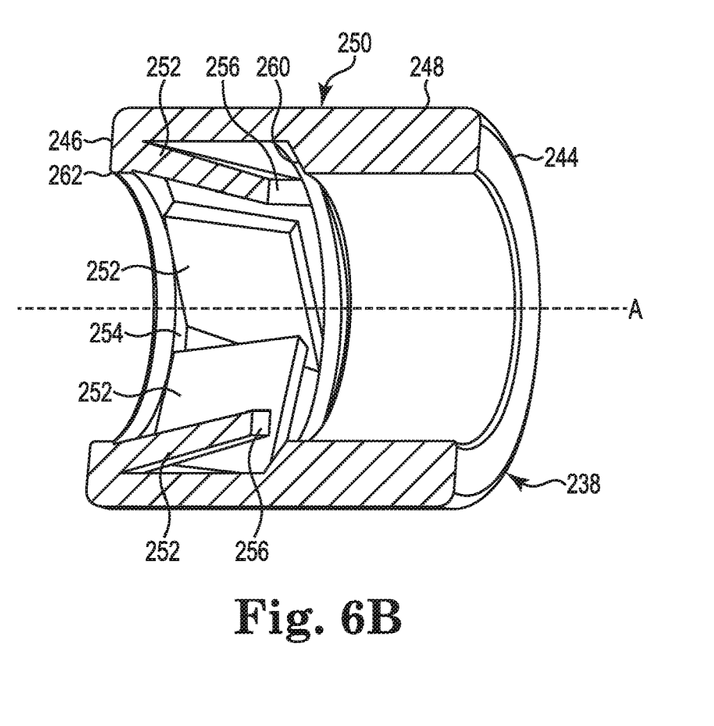

FIGS. 6A and 6B are a distal end view, and a cross-sectional view, respectively, of another electrical connector having spring contacts that are canted, in accordance with embodiments of the present invention. Together, FIGS. 6A and 6B show an electrical connector 238 including a proximal end 244, a distal end 246, a housing 250, and a plurality of spring contacts 252. The housing 250 may include an exterior surface 248, and the interior surface 254. The interior surface 254 may be in the form of a hollow cylinder having an axis A. The spring contacts 252 may project from the interior surface 254 of housing 250 and toward the proximal end 244 to a tip 256. As shown in FIGS. 6A and 6B, the spring contacts 252 may be blades that are canted. The canting of the spring contacts 252 may result in a larger deflection range over which the normal pressure applied by the spring contacts 252 is consistent. This feature might produce a more consistent contact resistance between the spring contacts 252 and the first terminal contact 26 in cases where a diameter of the first terminal contact 26 varies between the electrical leads 14.

In the embodiment of FIGS. 6A and 6B, the spring contacts 252 are illustrated as flat blades that are canted. However, it is understood that embodiments may also include curved blades that are canted. Such blades may offer increased contact area between the electrical connector 238 and the first terminal contact 26.

As further shown in FIGS. 6A and 6B, in some embodiments of the electrical connector 238, the housing 250 may further include a proximal end shoulder 260 and/or a distal end shoulder 262. The proximal end shoulder 260 may project radially inward toward the axis A between the tip 256 and the proximal end 244. The distal shoulder 262 may project radially inward toward the axis A at the distal end 246. The proximal end shoulder 260 and the distal end shoulder 262 may help align the electrical lead 14 within the electrical connector 238 and may prevent overstressing the spring contacts 252.

Embodiments of the electrical connector 238, including the housing 250 and the plurality of spring contacts 252 may be integrally formed such that the electrical connector 238 is a unitary structure. Such embodiments of the electrical connector 238 may be formed by an additive manufacturing process, such as, a powder bed fusion process as described below in reference to FIG. 8, or by another additive manufacturing process.

Figure 7A:
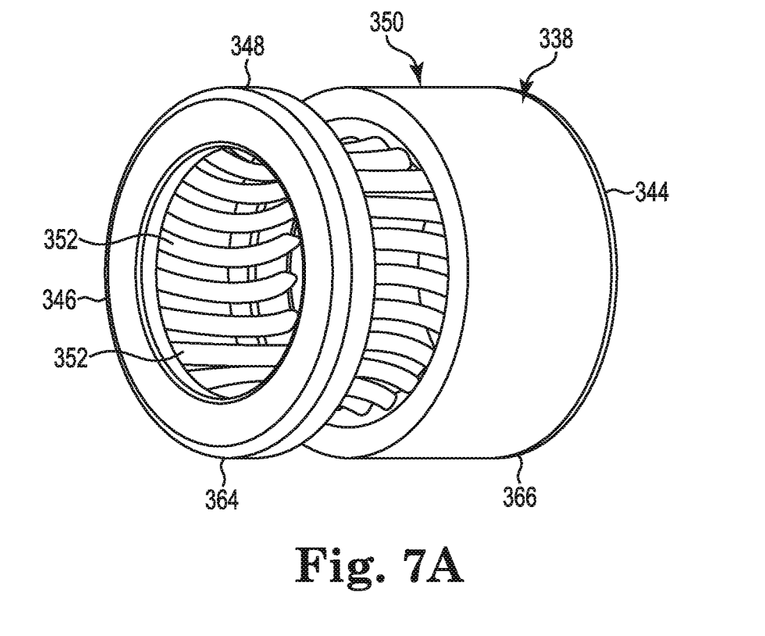
FIGS. 7A and 7B are a distal end view and a cross-sectional view, respectively, of another electrical connector in accordance with embodiments of the present invention.
Figure 7B:
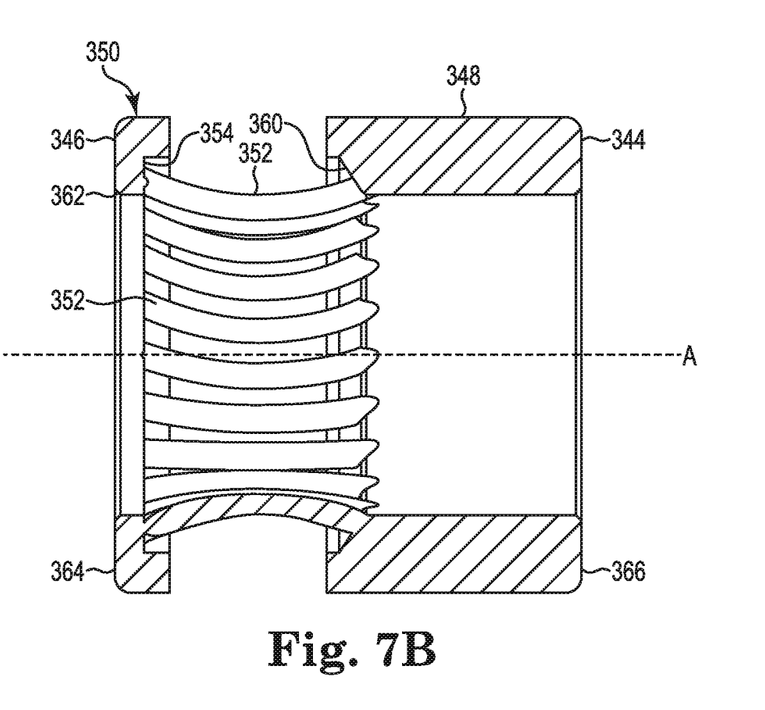

FIGS. 7A and 7B are a distal end view, and a cross-sectional view, respectively, of another electrical connector having spring contacts that are spiraled, in accordance with embodiments of the present invention. Together, FIGS. 7A and 7B show an electrical connector 338 including a proximal end 344, a distal end 346, a housing 350, and a plurality of spring contacts 352. The housing 350 may be in the form of a two-piece hollow cylinder having an axis A and include a distal portion 364 and a proximal portion 366. The distal portion 364 is axially apart from the proximal portion 366. The housing 350 may also include an exterior surface 348, an interior surface 354, a proximal end shoulder 360 and/or a distal end shoulder 362. The proximal end shoulder 360 may project radially inward toward the axis A from the proximal portion 366. The distal shoulder 362 may project radially inward toward the axis A from the distal portion 364 at the distal end 346. The proximal end shoulder 360 and the distal end shoulder 362 may help align the electrical lead 14 within the electrical connector 338.

As shown in FIGS. 7A and 7B, the spring contacts 352 may project from the interior surface 354 of the distal portion 364 and toward the proximal end 344 to connect with the proximal portion 366 at the proximal end shoulder 360. That is, the distal portion 364 and the proximal portion 366 may be connected to each other by the spring contacts 352. In some embodiments, spring contacts 352 may spiraled. The spiraling of the spring contacts 352 relative to the axis A may result in a longer physical contact region between each of the spring contacts 352 and the first terminal contact 26 inserted into the electrical connector 338. Also, the spiraling of the spring contacts 352 may result in a larger deflection range over which the normal pressure applied by the spring contacts 352 is consistent. This feature might produce a more consistent contact resistance between the spring contacts 352 and the first terminal contact 26 in cases where a diameter of the first terminal contact 26 varies between the electrical leads 14.

As with the spring contacts 52 described above for electrical connector 38, the spring contacts 352 may have an average cross-sectional aspect ratio along their length that is relatively low, such as 1, or 3, or between about 1 and about 3, and are thus more resistant to damage from being overstressed. The electrical connector 338 with the spring contacts 352 having an average cross-sectional aspect ratio along their length L that is relatively low, in combination with the proximal end shoulder 360 and/or the distal end shoulder 362, may be advantageously resistant to damage to the spring contacts 352. In addition, by separating the housing 350 into two portions physically apart, the distal portion 364 and the proximal portion 366, and connected to each other only by the spring contacts 352, the spring contacts 352 are able to flex, while both ends of the spring contacts 352 are physically supported. This arrangement may provide additional protection for the spring contacts 352.

Embodiments of the electrical connector 338, including the housing 350 and the plurality of spring contacts 352, may be integrally formed such that the electrical connector 338 is a unitary structure. Such embodiments of the electrical connector 338 may be formed by an additive manufacturing process, such as, a powder bed fusion process, as described below in reference to FIG. 8, or by another additive manufacturing process.

Figure 8:
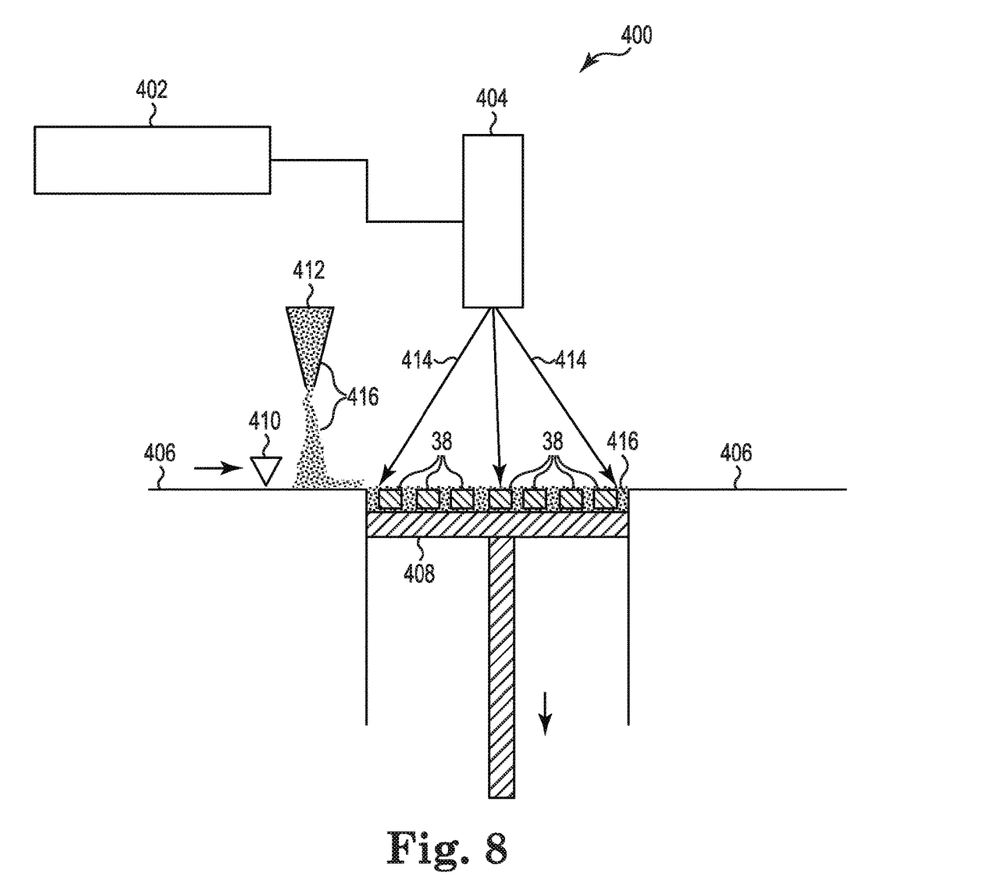
FIG. 8 is a schematic view of a system for additively manufacturing electrical connectors in accordance with embodiments of the present invention.

FIG. 8 is a schematic view of a powder bed fusion system for additively manufacturing electrical connectors, such as the electrical connector 38, the electrical connector 138, the electrical connector 238, and the electrical connector 338 in accordance with embodiments of the present invention. FIG. 8 illustrates an additive manufacturing system 400 including a controller 402, an energy beam source 404, a working surface 406, a moveable platform 408, a coating device 410, and a dispenser 412. The controller 402 may be a computing/controlling device controlling at least the energy beam source 404, the moveable platform 408, the coating device 410, and the dispenser 412. The energy beam source 404 may be any system able to generate an energy beam 414 and direct it to any position on the moveable platform 408. The energy beam 414 may be, for example, a laser beam or an electron beam. The moveable platform 408 may move vertically relative to working surface 406. The coating device 410 may move horizontally back and forth across the working surface 406 and the moveable platform 408 to sweep powder 416 dispensed from the dispenser 412 onto the moveable platform 408.

In operation, the controller 402 may direct the moveable platform 408 to be recessed from the working surface 406 by an amount equal to a desired layer thickness. The controller 402 may then direct the dispenser 412 to dispense a desired quantity of the powder 416 onto the working surface 406. The controller 402 may then direct the coating device 410 to sweep back and forth across the moveable platform 408 to deposit the powder 416 on to the moveable platform 408 at the desired layer thickness. The controller 402 may then direct the energy beam source 404 to generate the energy beam 414 at predetermined positions across the moveable platform 408 to sinter or fuse together the powder 416 at the predetermined positions. The predetermined positions across the moveable platform 408 correspond to the structure of a layer of the electrical connector 38. The controller 402 may then direct the moveable platform 408 to move down the desired thickness of the next layer and the previous steps may be repeated to produce another desired layer of the electrical connector 38. The preceding steps may be repeated multiple times as necessary as part of a method for manufacturing the electrical connector 38 in a layer-by-layer fashion in which the electrical connector 38 is integrally formed as a unitary structure. It is understood that the electrical connector 38 may also represent any of the electrical connector 138, the electrical connector 238, or the electrical connector 338 described above, or any other embodiment in accordance with the present invention. As shown in FIG. 8, a plurality of the electrical connectors 38 may be produced at the same time. It is also understood that a combination of various electrical connectors embodying the present invention may be manufactured together as described above.

In some embodiments, the powder 416 used to make the electrical connector 38 may be a metal powder having an average particle size of less than about 10 micrometers. In some embodiments, the powder 416 may be a metal powder having an average particle sized of about 5 micrometers. In other embodiments, the powder 416 may be a metal power having an average particle size less than 5 micrometers. Average particle size may be determined by a laser diffraction based particle size analyzer, for example, a Malvern® Mastersizer 2000™. Employing metal powders having average particle sizes of about 5 micrometers, or less than about 10 micrometers and in which the energy beam 414 is a laser beam may be referred to as micro-laser sintering. Dimensional and morphological control of the additive manufacturing of the electrical connector 38 may be enhanced with micro-laser sintering. The powder 416 may also be, for example, a stainless steel (e.g., 316L), a platinum/iridium alloy, silver, or titanium. The powder 416 may also be, for example, a nickel/cobalt/chromium alloy including about 34 to 36 wt. % nickel, about 19 to 21 wt. % chromium, about 9 to 11 wt. % molybdenum, and about 32 to 38 wt. % cobalt. In some embodiments, the powder 416 may consist essentially of 34 to 36 wt. nickel, 19 to 21 wt. % chromium, 9 to 11 wt. % molybdenum, and 32 to 38 wt. % cobalt.

Additive manufacturing of a metal part, such as the electrical connector 38 may result in a surface finish that is, in some locations, more textured than desired. In some embodiments the method manufacturing the electrical connector 38 may further include finishing at least a portion of any surfaces of the electrical connector 38. For example, it may be beneficial to electrochemically polish surfaces of the plurality of spring contacts 52 and the interior surface 54, but not the exterior surface 48. Additionally or alternatively, other finishing processes may be employed including mechanical polishing, electro plasma polishing, glazing, wet blasting, grit blasting, and wire electrical discharge machining. In some embodiments, passivating techniques may also be employed to remove stray impurities from the surface, such as iron.

Although the housing 50 shown in FIGS. 2, 3A, 3B, 4A and 4B as a featureless structure, it is understood that features may be added. For example, a structure may be added to the external surface 48 to enhance an electrical connection between the electrical connector 38 and the connection wire 42. In another example, portions of the housing 50 may be omitted to the extent that the conductivity and strength of electrical connector 38 remains sufficient for its intended purpose. Such examples may include a series of holes between the exterior surface 48 and the interior surface 54. Reducing the metal volume of the electrical connector 38 in this fashion may reduce the time required to additively manufacture the electrical connector 38.

For the sake of brevity, embodiments have been described above in reference to the electrical connector 38 (or 138, 238, or 338) configured to form an electrical connection with the first terminal contact 26 of the electrical lead 14. However, it is understood that the electrical connector 40 configured to form an electrical connection with the second terminal contact 28 may also embody the present invention.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An electrical connector for detachably connecting an electrical lead to an implantable medical device, the connector comprising:
   a conductive housing extending from a proximal end to a distal end, the conductive housing having an interior surface forming a hollow cylinder; and
   a plurality of spring contacts projecting from the interior surface of the conductive housing, wherein at least one spring contact of the plurality of spring contacts extends from the interior surface, along a length of the conductive housing in a direction toward the proximal end, to a tip, wherein a portion of the at least one spring contact along the length of the conductive housing extends toward a longitudinal axis of the conductive housing, and wherein the plurality of spring contacts is at least partially contained within the conductive housing and configured to form an electrical connection to an electrical lead inserted within the conductive housing;
   wherein the conductive housing and the plurality of spring contacts are integrally formed by an additive manufacturing process such that the electrical connector is a unitary structure.

2. The electrical connector of claim 1, wherein the each spring contact of the plurality of spring contacts has an average cross-sectional aspect ratio along its length, wherein the average cross-sectional aspect ratio is about 1 to about 3.

3. The electrical connector of claim 2, wherein the average cross-sectional aspect ratio is about 1.

4. The electrical connector of claim 1, wherein the additive manufacturing process is a powder bed fusion process employing a metal powder, wherein the metal powder is an alloy including about 34 to 36 wt. % nickel, about 19 to 21 wt. % chromium, about 9 to 11 wt. % molybdenum, and about 32 to 38 wt. % cobalt.

5. The electrical connector of claim 1, wherein each spring contact of the plurality of spring contacts has an elliptical cross-sectional shape along at least a portion of its length.

6. The electrical connector of claim 1, wherein each spring contact of the plurality of spring contacts has a triangular cross-sectional shape along at least a portion of its length.

7. The electrical connector of claim 1, wherein the plurality of spring contacts includes at least twenty spring contacts.

8. The electrical connector of claim 1, wherein the conductive housing further includes:
a distal portion adjacent to the distal end; and
a proximal portion adjacent to the proximal end and spaced apart from the distal portion;
wherein the plurality of spring contacts projects from the interior surface of the distal portion of the conductive housing and toward the proximal end, and the proximal portion is connected to the distal portion by the plurality of spring contacts.

9. The electrical connector of claim 1, wherein each spring contact of the plurality of spring contacts is canted or spirals at least partially around an axis of the conductive housing.

10. An implantable medical device comprising:
a case including:
operational circuitry for providing therapy; and
an electrical feedthrough electrically connected to the circuit; and
a lead connector block attached to the housing at the electrical feedthrough, the lead connector block configured to receive at least one terminal pin of an electrical lead, the terminal pin including at least one terminal pin contact, the lead connector block including:
an electrical connector electrically connected to the electrical feedthrough for detachably connecting the operational circuitry to the electrical lead, the connector including:
a conductive housing extending from a proximal end to a distal end, the conductive housing having an interior surface forming a hollow cylinder; and
a plurality of spring contacts projecting from the interior surface of the conductive housing, wherein at least one spring contact of the plurality of spring contacts extends from the interior surface, along a length of the conductive housing, to a tip positioned toward the proximal end, wherein a portion of the at least one spring contact along the length extends toward a longitudinal axis of the conductive housing, and wherein the plurality of spring contacts is at least partially contained within the conductive housing and configured to form the electrical connection to the terminal pin contact of the electrical lead inserted within the conductive housing;
wherein the conductive housing and the plurality of spring contacts are integrally formed by an additive manufacturing process such that the electrical connector is a unitary structure.

11. The device of claim 10, wherein each spring contact of the plurality of spring contacts has an average cross-sectional aspect ratio along its length, wherein the average cross-sectional aspect ratio is about 1 to about 3.

12. The device of claim 10, wherein the additive manufacturing process is a powder bed fusion process employing a metal powder, wherein the metal powder is an alloy including about 34 to 36 wt. % nickel, about 19 to 21 wt. % chromium, about 9 to 11 wt. % molybdenum, and about 32 to 38 wt. % cobalt.

13. The device of claim 10, wherein each spring contact of the plurality of spring contacts has has an elliptical cross-sectional shape along at least a portion of its length.

14. The device of claim 10, wherein the plurality of spring contacts includes at least twenty spring contacts.

* * * * *